US00PP32044P2

(12) United States Plant Patent
Egger

(10) Patent No.: US PP32,044 P2
(45) Date of Patent: Aug. 4, 2020

(54) ***HUECHERA* PLANT NAMED 'TNHEUNESI'**

(50) Latin Name: ***Heuchera* hybrid**
Varietal Denomination: TNHEUNESI

(71) Applicant: Terra Nova Nurseries, Inc., Canby, OR (US)

(72) Inventor: Janet N. Egger, Seattle, WA (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 16/602,008

(22) Filed: Jul. 18, 2019

(51) Int. Cl.
*A01H 5/12* (2018.01)
*A01H 6/80* (2018.01)

(52) U.S. Cl.
USPC ..... Plt./440

(58) Field of Classification Search
USPC ..... Plt./440
CPC . A01H 5/02; A01H 5/12; A01H 5/025; A01H 6/80; A01H 5/00; A01H 6/14
See application file for complete search history.

(56) References Cited

PUBLICATIONS

Terra Nova Nurseries, Inc. Heuchera Northern Exposure Sienna, retrieved on Mar. 5, 2020, retrieved from the Internet at http://www.terranovanurseries.com/product/heuchera-northern-exposure-sienna/, 3 pp. (Year: 2020).*

Vellekoop Terra Nova introduces their hardiest ornamental series "Foolproof varieties are always on-trend" 2019, retrieved on Mar. 5, 2020, retrieved from the Internet at http://www.terranovanurseries.com/product/heuchera-northern-exposure-sienna/, 2 pp. (Year: 2019).*

* cited by examiner

*Primary Examiner* — June Hwu
(74) *Attorney, Agent, or Firm* — Klarquist Sparkman, LLP

(57) ABSTRACT

A new and distinct *Heuchera* plant characterized by lime green leaves with dark orange veins in cold weather changing to orange-red centers in warm temperatures, medium tall, upright flowering stems with dark pink flowers, medium size, slightly lobed, geranium-like leaves, good sun and shade tolerance, a medium-large, mounding habit with excellent crown count, and excellent vigor.

1 Drawing Sheet

Botanical denomination: *Heuchera* hybrid.
Variety designation: 'TNHEUNESI'.
Trademark Designation: NORTHERN EXPOSURE™ Sienna.

BACKGROUND OF THE INVENTION

The present invention relates to a new and distinct cultivar of *Heuchera* given the cultivar name of 'TNHEUNESI'. *Heuchera* is in the family Saxifragaceae. *Heuchera* 'TNHEUNESI' originated as a controlled cross using *Heuchera* 'B104-2', a proprietary, unpatented, unnamed plant as the seed parent, and *Heuchera* 'B98-1', a proprietary, unpatented, unnamed plant as the pollen parent. These parents are a result of breeding using hardy *Heuchera richardsonii* crossed with proprietary hybrid lines. *Heuchera* 'TNHEUNESI' was bred to be a hardy, large, landscape plant.

Compared to the seed parent, *Heuchera* 'B104-2', the new cultivar has pink flowers rather than red.

Compared to the pollen parent, *Heuchera* 'B98-1', the new cultivar has a larger habit and no veil.

Compared to *Heuchera* 'Delta Dawn', U.S. Plant Pat. No. 23,545, the new cultivar has taller flowering stems with dark pink flowers rather than short flowering stems and cream white flowers. The new cultivar has smaller leaves and a higher crown count.

Compared to *Heuchera* NORTHERN EXPOSURE™ Amber ('TNHEUNEA'), U.S. Plant Pat. No. 29,397, the new cultivar has green leaves and dark veins in cold temperatures rather than yellow-orange and light colored margins of yellow tones. The new cultivar has dark pink flowers rather than yellow green flowers.

This new *Heuchera* is uniquely distinguished by:

1. lime green leaves with dark orange veins in cold weather changing to orange-red centers in warm temperatures,
2. medium tall, upright flowering stems with dark pink flowers,
3. medium size, slightly lobed, geranium-like leaves,
4. good sun and shade tolerance,
5. a medium-large, mounding habit with excellent crown count, and
6. excellent vigor.

This new cultivar has been reproduced only by asexual propagation (tip cuttings and tissue culture using growing tips). Each of the progeny exhibits identical characteristics to the original plant. Asexual propagation by cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may change with variations in environment without a change in the genotype of the plant.

BRIEF DESCRIPTION OF THE DRAWINGS

FIG. 1 shows a twelve-month-old plant of *Heuchera* 'TNHEUNESI' growing in the field in full sun in May in Canby, Oreg.

FIG. 2 shows a nine-month-old plant of *Heuchera* 'TNHEUNESI' growing in a one-gallon pot in full sun in late October in Canby, Oreg.

DETAILED PLANT DESCRIPTION

The following is a detailed description of the new *Heuchera* cultivar based on observations taken in October of a nine-month-old specimen growing in the trial field in part shade in Canby, Oreg. Canby is Zone 8 on the USDA Hardiness map. Temperatures range from a high of 95° F. in August to an average of 32° F. in January. Normal rainfall in Canby is 42.8 inches per year. The color descriptions are all based on The Royal Horticultural Society Colour Chart, 5$^{th}$ edition, 2007.

Plant:

*Form.*—Basal rosette, herbaceous perennial.
*Hardiness.*—USDA Zone 3 to 9.
*Size.*—17 cm tall from ground to foliage, 55 cm tall from ground to top of flowers, 30 cm wide.
*Number of crowns.*—About 25.
*Habit.*—Medium-large, mounding.
*Vigor.*—Excellent.

Leaf:

*Type.*—Simple.
*Arrangement.*—Rosette.
*Shape.*—Broadly ovate to orbicular.
*Number.*—About 230.
*Blade size.*—Grows to 10.5 cm long and 9 cm wide.
*Venation.*—Palmate.
*Lobing /Division.*—7 shallow palmate lobes.
*Margins.*—Crenate, slightly undulate; leaf margin indentations, medium; depth of indentations, medium.
*Apex.*—Mucronulate.
*Base.*—Cordate, strongly overlapping and often spiraling in.
*Surface texture.*—Glandular-puberulent on both sides.
*Leaf rugosity.*—Absent.
*Petiole description.*—Grows to 20 cm long and 4 mm wide, glandular hairs, Yellow Green 144C.
*Leaf color.*—Mature leaves in warm temperatures: top side Greyed Orange 172B in center, veins blending to Yellow Green 151C, margins Yellow Green 144B, bottom side in center and veins Greyed Orange 172D blending to Yellow Green 144D; leaves in cool temperatures: top side between Green 137B and Yellow Green 144A and veins between Greyed Orange 173A and Greyed Orange 173B, bottom side closest to Greyed Green 194B and veins Greyed Green 195B.
*Leaf color.*—Immature leaves, lower surface 162B; upper leaf surface 153D.
*Leaf glossiness.*—Weak.

Inflorescence:

*Size.*—Grows to 12.5 cm wide and 16 cm long.
*Type.*—Thyrse, strong, upright.
*Number of thyrse.*—Up to 75.
*Number of flowers per thyrse.*—85.
*Peduncle.*—Grows to 29 cm long and 5 mm wide at base, glandular hairs, bottom ⅔ closest to Yellow Green 144C blending to Yellow Green 144C strongly tinted with Greyed Orange 176C.
*Pedicel.*—Grows to 4 mm long, with glandular hairs, Greyed Purple 187C.
*Bloom period.*—Late May to frost in Canby, Oreg.
*Density of flowers.*—Within the inflorescence, sparse.

Flower bud:

*Size.*—4 mm wide and 6 mm long.
*Description.*—Glandular-puberulent, ovoid, down facing.
*Color.*—Closest to Red Purple 61C.

Flower:

*Type.*—Perfect.
*Shape.*—Campanulate.
*Attitude.*—Down and side-facing.
*Size.*—8 mm long and 6 mm wide.
*Corolla description.*—5 petals, each 2 mm long and 0.5 mm wide, spatulate, margins entire, tip acute, glandular-puberulent on outside, glabrous on inside, both sides Red Purple 59C.
*Calyx description.*—Campanulate, 8 mm long and 5 mm wide, with 5 lobes with narrow sinuses divided halfway to the base, each 3 mm wide and 2.5 mm long, oblong in shape, back side glandular-puberulent with glandular hairs, glabrous inside, tip obtuse, margin entire, both sides closest to Red Purple 61B tinted Red Purple 59B on tips.
*Stamen description.*—5 in number, filaments 1.5 mm long, White NN155C, anthers 0.5 mm long, Greyed Orange 167B.
*Pollen.*—Sparse.
*Pistil description.*—1, 2-beaked, 8 mm long and 2 mm wide, White 155D overall, ovary 4.5 mm long and 2.5 mm wide, style 4 mm long.
*Fragrance.*—None.
*Lastingness.*—Each thyrse blooms for about 3 weeks on the plant.

Fruit and seed: None seen.

Pest and disease tolerance: The new cultivar is typical to the genus. No known resistances to pests or diseases. No problems have been found in Canby, Oreg.

I claim:

1. A new and distinct *Heuchera* plant as herein illustrated and described.

* * * * *

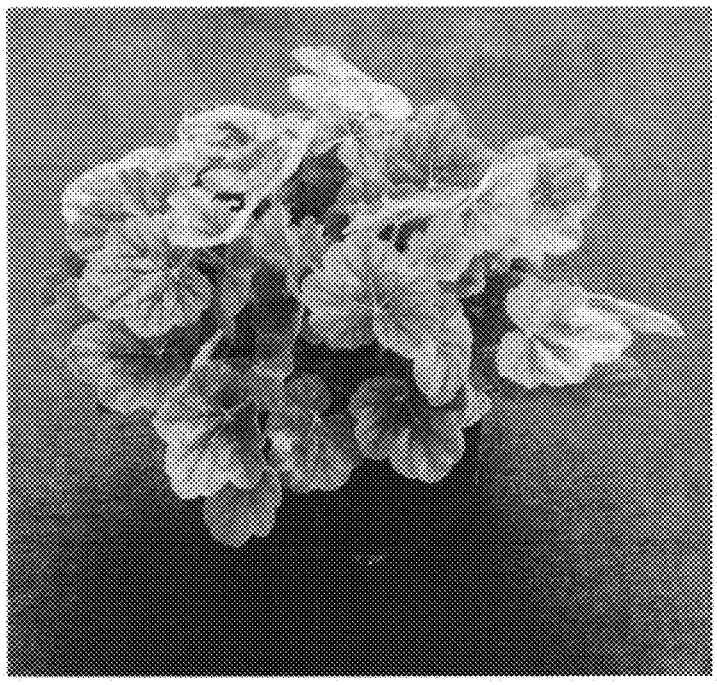

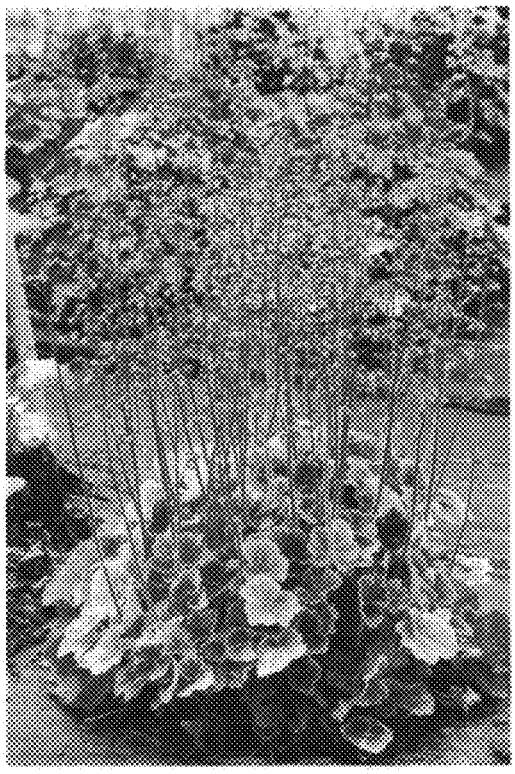
Fig. 1 Left
Fig. 2 Below